United States Patent
Martin et al.

(10) Patent No.: US 9,201,081 B2
(45) Date of Patent: Dec. 1, 2015

(54) PC-O 44:6—A BIOMARKER FOR VISCERAL ADIPOSITY

(71) Applicant: Nestec S.A., Vevey (CH)

(72) Inventors: Francois-Pierre Martin, Vuisternens-devant-Romont (CH); Ivan Montoliu Roura, Lausanne (CH); Philippe Alexandre Guy, Lucens (CH); Serge Andre Dominique Rezzi, Semsales (CH)

(73) Assignee: NESTEC S.A., Vevey (CH)

( * ) Notice: Subject to any disclaimer, the term of this patent is extended or adjusted under 35 U.S.C. 154(b) by 0 days.

(21) Appl. No.: 14/552,944

(22) Filed: Nov. 25, 2014

(65) Prior Publication Data
US 2015/0080264 A1    Mar. 19, 2015

Related U.S. Application Data

(63) Continuation of application No. PCT/EP2013/061874, filed on Jun. 10, 2013.

(30) Foreign Application Priority Data

Jun. 12, 2012 (EP) .................. 12171569

(51) Int. Cl.
*G01N 33/92* (2006.01)
*G01N 33/48* (2006.01)

(52) U.S. Cl.
CPC .............. *G01N 33/92* (2013.01); *G01N 33/48* (2013.01); *G01N 2405/04* (2013.01); *G01N 2800/044* (2013.01); *Y10T 436/24* (2015.01)

(58) Field of Classification Search
CPC ...... Y10T 436/24; G01N 33/48; G01N 33/68; G01N 33/6806; G01N 33/6848; G01N 33/92; G01N 2570/00; G01N 2800/00; G01N 2800/02; G01N 2800/044; G01N 2800/32; G01N 2800/50; G01N 2405/04

USPC .................. 436/63, 71, 86, 89, 173; 435/29; 554/80; 73/61.43; 558/169
See application file for complete search history.

(56) References Cited

U.S. PATENT DOCUMENTS

| | | | |
|---|---|---|---|
| 2012/0129265 A1* | 5/2012 | Lundin et al. ................. | 436/89 |
| 2012/0202240 A1* | 8/2012 | Deigner et al. ................ | 435/29 |
| 2012/0326025 A1* | 12/2012 | Weinberger et al. .......... | 250/282 |
| 2015/0075262 A1 | 3/2015 | Martin et al. | |
| 2015/0096357 A1 | 4/2015 | Martin et al. | |

FOREIGN PATENT DOCUMENTS

| | | |
|---|---|---|
| EP | 2172775 A1 | 4/2010 |
| EP | 2249161 A1 | 11/2010 |

OTHER PUBLICATIONS

Hu, C. et al., "Analytical strategies in lipidomics and applications in disease biomarker discovery," Journal of Chromatography B: Biomedical Sciences & Applications, 877(26):2836-2846, 2009.
Oberbach, A. et al., "Combined proteomic and metabolomic profiling of serum reveals association of the complement system with obesity and identifies novel markers of body fat mass changes," Journal of Proteome Research, 10(10):4769-4788, 2011.
Romisch-Margl, W. et al., "Procedure for tissue sample preparation and metabolite extraction for high-throughput targeted metabolomics," Metabolomics, 8(1):133-142, 2011.

* cited by examiner

*Primary Examiner* — Maureen Wallenhorst
(74) *Attorney, Agent, or Firm* — Kilpatrick Townsend & Stockton LLP

(57) ABSTRACT

The present invention generally relates to the field of biomarkers. In particular, the present invention relates to biomarkers such as PC-O 44:6 that can be used, for example for detecting and/or quantifying visceral adiposity and/or changes in visceral adiposity. This biomarker may also be used to diagnosing the effect of a change in lifestyle on visceral adiposity in a subject.

9 Claims, 5 Drawing Sheets

PC-O 44:6—A BIOMARKER FOR VISCERAL ADIPOSITY

Figure 1:
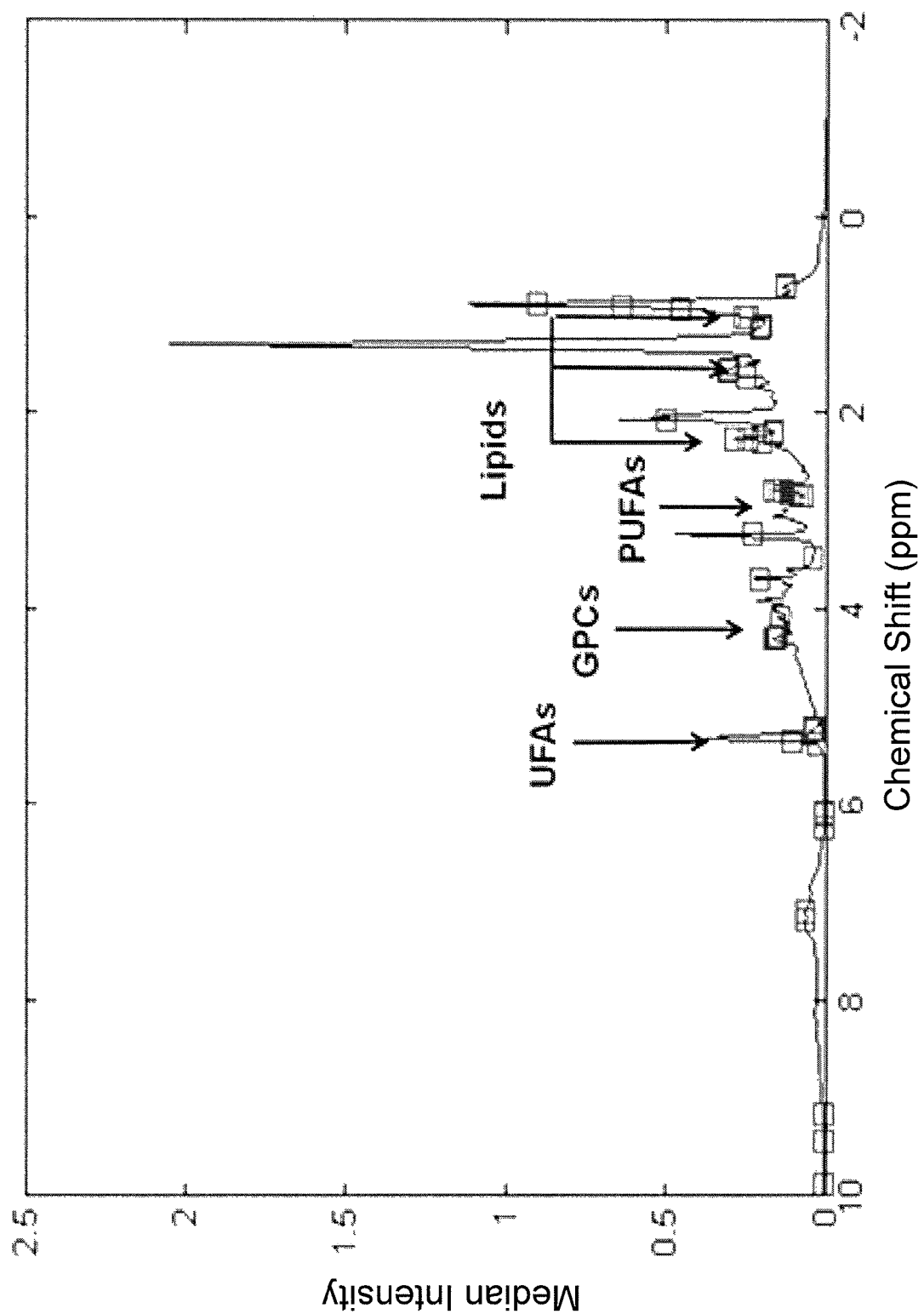

The present application is a continuation of PCT/EP2013/061874, filed Jun. 10, 2013, which application claims priority to European Application No. 12171569.2, filed Jun. 12, 2012, the disclosures of which are hereby incorporated by reference in their entirety for all purposes.

The present invention generally relates to the field of biomarkers. In particular, the present invention relates to biomarkers such as 1-O-alkyl-2-acylglycerophosphocholine (PC-O) 44:6 that can be used, for example for detecting and/or quantifying visceral adiposity and/or changes in visceral adiposity. This biomarker may also be used for diagnosing the effect of a change in lifestyle on visceral adiposity in a subject.

The continuous rise in the overweight and obesity epidemic, particularly among children, has made the deciphering of their associated genome and metabolome phenotypes become one of the greatest public health challenges. Although malnutrition and obesity, as defined by body mass index (BMI), impose a substantial toll on life expectancy, it is clear that BMI has considerable limitations in the assessment of body composition and lack sensitivity for assessing disease risks (Dulloo, A. G., et al. (2010) Int. J. Obes. (Lond) 34 Suppl 2, S4-17. Dullo et al. recently reviewed recent advances in concepts about health risks related to body composition phenotypes, including (i) the partitioning of BMI into a fat mass (FM) index (FM/H2) and a fat-free-mass (FFM) index (FFM/H2), (ii) the partitioning of FFM into organ mass and skeletal muscle mass, (iii) the partitioning of FM into hazardous fat and protective fat and (iv) the interplay between adipose tissue expandability and ectopic fat deposition within or around organs/tissues that constitute the lean body mass (Dulloo, A. G., et al. (2010) Int. J. Obes. (Lond) 34 Suppl 2, S4-17)

During the last decades, numerous investigations using state of the art technologies have identified genes and transcription factors associated with fat storage and obesity (Viguerie, N., et al. (2005) Diabetologia 48, 123-131; Viguerie, N., et al. (2005) Biochimie 87, 117-123; Sorensen, T. I. et al. (2006) PLoS. Clin. Trials 1, e12; Klannemark, M., et al. (1998) Diabetologia 41, 1516-1522; Clement, K. et al. (2007) J. Intern. Med. 262, 422-430), genetic inheritability (Teran-Garcia, M. Et al. (2007) Appl. Physiol Nutr. Metab 32, 89-114) and have suggested an influence of the human gut microbiota on obesity incidence (Backhed, F., et al. (2007) Proc. Natl. Acad. Sci. U.S.A. 104, 979-984; Ley, R., et al. (2006) Nature 444, 1022-1023; Turnbaugh, P., et al. (2006) Nature 444, 1027-1031).

However, under similar obesogenic and diabetogenic environments, many individuals still remain metabolically healthy and resistant to adiposity-associated cardiovascular disease (CVD) risks. In addition to the awareness that disease risks associated with obesity may not be uniform (Wildman, R. P., et al., (2008) Arch. Intern. Med. 168, 1617-1624), an increasing number of individuals with normal weight (body mass index, BMI<25) express cardiometabolic abnormalities previously thought to be specific to overweight and obese states. Most recent evidence indicates how regio-specific body composition may determine individual predisposition to metabolic disease, with body fat and in particular visceral fat distribution being correlated with increased risk of cardiometabolic disorders, diabetes, hypertension, nonalcoholic fatty liver disease, and mortality.

Visceral adiposity is been clinically monitored using waist and hip measurements, (e.g. >0.9 for men and >0.85 for women, which however suffers from similar limitations especially in obese populations. Gold standard imaging technologies, including magnetic resonance imaging (MRI) and computed tomography (CT) scans, now generate regio-specific and highly accurate quantification of visceral fat depots. However, the assessment of the metabolism associated with visceral fat remains particularly challenging due to the lack of non-invasive, fast and reliable biomarkers that can be used in epidemiological studies and due to limitations of conventional analytical approaches that are not suited for the holistic analysis of the metabolism.

Excess fat stored in the trunk or android regions could be metabolically less healthy than fat stored in the gynoid area, with insulin resistance as a key causal mechanism. Therefore, patient stratification is necessary for personalized nutritional and therapeutical management, yet its application is challenged when subjects have similar waist-to-hipp ratio and access to imaging facilities is limited. There is therefore and urgent need for biomarkers that allow assessing the presence of visceral fat, the metabolism associated with visceral fat and/or changes therein in a simple and reliable way.

The present inventors have addresses this need.

It was therefore the objective of the present invention to improve the state of the art and to provide biomarkers that meet the objective of the present invention and/or that allow overcoming at least one of the disadvantages of the present state of the art.

To identify appropriate biomarkers the inventors have used a metabonomic approach.

Metabonomics is considered today a well-established system approach to characterize the metabolic phenotype, that comprises the influence of various factors such as environment, drugs, dietary, lifestyle, genetics, and microbiome factors. Unlike gene expression and proteomic data that indicate the potential for physiological changes, metabolites and their dynamic concentration changes within cells, tissues and organs, represent the real end-points of physiological regulatory processes.

Recently, metabolomics and lipidomics-based discoveries have been accelerating our understanding of disease processes, and will provide novel avenues for prevention and nutritional management of the sub-clinical disorders associated to metabolic syndrome.

The present inventors have aimed to provide a comprehensive metabolic phenotype of a regio-specific body composition: visceral adiposity. This has allowed the identification of biological markers specific of visceral adiposity.

In the present study, the metabolism associated with visceral adiposity was investigated in a cohort of 40 healthy obese women using the measurement of various metabolic endpoints in combination with in vivo quantification of body composition using Dual energy X-ray Absorptiometry (DXA) and abdominal fat distribution using computerized tomography (CT) scan.

Using a combination of proton nuclear magnetic resonance ($^1$H NMR) spectroscopy and targeted LC-MS/MS profiles of plasma and 24 hour urine samples collected overtime, the inventors have identified novel metabolic biomarkers of visceral fat distribution in this well defined obese cohort with different visceral fat deposition patterns.

As such, the inventors have identified a novel biomarker, PC-O 44:6.

PC-O is 1-O-alkyl-2-acylglycerophosphocholine.

The individual lipid species were annotated as follows: [lipid class] [total number of carbon atoms]:[total number of double bonds]. For example, PC 34:1 reflects a phosphatidylcholine species comprising 34 carbon atoms and 1 double bond.

PC-O 44:6 is therefore 1-O-alkyl-2-acylglycerophosphocholine 44:6.

The inventors have further found that PC-O 44:6 may be used as a biomarker for detecting and/or quantifying visceral adiposity and/or changes in visceral adiposity. This diagnostic method is practised outside of the human or animal body.

This detection and/or quantification of the biomarker may be carried out in a body liquid. The body liquid may be blood, blood plasma, blood serum or urine, for example.

Typically, the biomarker detection and/or quantification step is carried out in a body fluid sample that was previously obtained from the subject to be tested.

Visceral fat is also known as abdominal fat, organ fat or intra-abdominal fat, and is located inside the abdominal cavity in between organs.

Visceral fat may be composed of several adipose depots, including mesenteric, epididymal white adipose tissue (EWAT), and perirenal depots, as well as epicardial adipose tissue and fat around liver and stomach. Typically, fat in the abdomen is mostly visceral, often resulting in the famous "beer belly".

Too much visceral fat results in central obesity, which in turn is linked to cardiovascular disorders, type 2 diabetes, insulin resistance, or inflammatory diseases, for example.

These are examples of disorders associated with excess visceral fat.

The present invention relates also to a method of diagnosing visceral adiposity in a subject, comprising determining the level of 1-O-alkyl-2-acylglycerophosphocholine (PC-O) 44:6 in a body fluid sample previously obtained from a subject to be tested, and comparing the subject's PC-O 44:6 level to a predetermined reference value, wherein the predetermined reference value is based on an average PC-O 44:6 level in the same body fluid in a control population, and wherein a decreased PC-O 44:6 level in the sample compared to the predetermined reference value indicates an increased visceral adiposity.

Visceral adiposity may include mesenteric, epididymal white adipose tissue and/or perirenal fat, as well as epicardial adipose tissue and fat around liver and stomach.

The body fluid may be blood, blood serum, blood plasma, or urine, for example.

Blood serum and/or blood plasma have the advantage that the signal to noise ratio for the biomarker to be tested is particularly high.

Urine has the advantage that the body fluid sample can be obtained non-invasively.

Irrespective of the chosen body fluid, the method of the present invention has the advantage that obtaining such body fluids from a subject is a well established procedure.

The actual diagnosis method is then carried out in a body fluid sample outside the body.

The level of PC-O 44:6 in the sample can be detected and quantified by any means known in the art. For example, mass spectroscopy, e.g, UPLC-ESI-MS/MS, may be used. Other methods, such as other spectroscopic methods, chromatographic methods, labeling techniques, or quantitative chemical methods may be used as well.

Ideally, the PC-O 44:6 level in the sample and the reference value are determined by the same method.

The predetermined reference value may be based on an average PC-O 44:6 level in the tested body fluid in a control population. The control population can be a group of at least 3, preferably at least 10, more preferred at least 50 people with a similar genetic background, age and average health status.

The control population can also be the same person, so that the predetermined reference value is obtained previously from the same subject. This will allow a direct comparison of the effect of a present lifestyle to a previous lifestyle on visceral adiposity, for example, and improvements can be directly assessed.

The determination of visceral fat adiposity allows concluding on the presence of visceral fat adiposity and on the risk to acquire associated disorders.

The subject matter of the present invention also relates to a method of diagnosing a change in visceral adiposity in a subject, comprising determining the level of PC-O 44:6 in a body fluid sample previously obtained from a subject to be tested, and comparing the subject's PC-O 44:6 level to a predetermined reference value, wherein the predetermined reference value is based on a PC-O 44:6 level in the same body fluid obtained from the same subject previously, and wherein a decreased PC-O 44:6 level in the sample compared to the predetermined reference value indicates increased visceral adiposity.

This method allows following the build-up or reduction of visceral fat over time, and consequently allows conclusions on increased or decreased risks to develop disorders associated with visceral adiposity.

This has for example the advantage that immediate results are available, long before an actual increase or decrease of visceral fat can be determined. This is in particular good for the motivation of people that aim to reduce visceral fat. Notably, the reduction of visceral fat is a difficult task often requiring intensive exercise. Ohkawara et al. suggests at least 10 metabolic equivalent of task (MET)-hours per week of aerobic exercise are required for effective visceral fat reduction (Ohkawara, K.; et al., (2007), International journal of obesity (2005) 31 (12): 1786-1797).

The present invention also relates to a method of diagnosing the effect of a change in lifestyle on visceral adiposity in a subject, comprising determining the level of PC-O 44:6 in a body fluid sample previously obtained from a subject to be tested, and comparing the subject's PC-O 44:6 level to a predetermined reference value, wherein the predetermined reference value is based on a PC-O 44:6 level in the same body fluid obtained from the same subject previously, and wherein a decreased PC-O 44:6 level in the sample compared to the predetermined reference value indicates a positive effect of the change in lifestyle on visceral adiposity.

This method has the effect that it allows monitoring the effect of lifestyle changes on visceral fat mass and on risks for associated disorders.

The change in lifestyle may be any change, such as a new job, a different stress level, a new relationship, increases or decreases in physical activity, and/or a change in overall wellbeing.

For example, the change in lifestyle may be a change in the diet.

The change in diet may be an increase or decrease in carbohydrate, lipid and/or protein content. It may be the switch to a different regional diet, such as the Mediterranean diet, for example. It may also be a change in total caloric intake.

As such the method of the present invention may be used to test the effectiveness of a new nutritional regimen, of nutritional products and/or of medicaments.

Nutritional products may be for example products that claim to have an effect on body fat, weight management and/or visceral fat.

Typically, nutritional products may be food products, drinks, pet food products, food supplements, nutraceuticals, food additives or nutritional formulas.

For example, the change in the diet may be the use of at least one nutritional product that was previously not consumed or consumed in different amounts.

As such, the method of the present invention may be used to test the effectiveness of a new nutritional regimen and/or a nutritional product.

PC-O 44:6 may be used as the only marker for the purpose of the present invention.

While PC-O 44:6 as sole marker is effective as a tool for the diagnosis method of the present invention, the quality and/or the predictive power of said diagnosis will be improved, if the diagnosis relies on more than just one marker.

Hence one or more other markers for diagnosing visceral adiposity and/or the risk for associated disorders in a subject may be used in combination with PC-O 44:6.

The inventors were surprised to see that also other biomarkers can be used to detect diagnosing visceral adiposity and/or the risk for associated disorders.

As such the inventors have identified that decreased body fluid concentrations of PC-O 44:6, PC-O 44:4, PC-O 42:4, PC-O 40:4, and/or PC-O 40:3; and/or increased body fluid concentrations of tyrosine and/or glutamine allow diagnosing an increase in visceral fat amounts and/or an increased risk for developing disorders associated with excess visceral fat.

Conversely, increased body fluid concentrations of PC-O 44:6, PC-O 44:4, PC-O 42:4, PC-O 40:4, and/or PC-O 40:3; and/or decreased body fluid concentrations of tyrosine and/or glutamine allow diagnosing a decrease in visceral fat amounts and/or a reduced risk for developing disorders associated with excess visceral fat.

The methods of the present invention may, hence, further comprise the steps of determining the level of at least one further biomarker selected from the group consisting of glutamine, and/or tyrosine, PC-O 44:4, PC-O 42:4, PC-O 40:4, and/or PC-O 40:3 in the body fluid sample, and comparing the subject's level of at least one of glutamine, and/or tyrosine, PC-O 44:4, PC-O 42:4, PC-O 40:4, and/or PC-O 40:3 to a predetermined reference value, wherein the predetermined reference value is based on average glutamine, tyrosine, PC-O 44:4, PC-O 42:4, PC-O 40:4, and/or PC-O 40:3 levels in a body fluid sample of a normal healthy control population, or on glutamine, tyrosine, PC-O 44:4, PC-O 42:4, PC-O 40:4, and/or PC-O 40:3 levels in the same body fluid obtained from the same subject previously, and wherein an increased glutamine and/or tyrosine level and/or a decreased PC-O 44:6, PC-O 44:4, PC-O 42:4, PC-O 40:4, and/or PC-O 40:3 level in the body fluid sample compared to the predetermined reference values indicates an increased visceral adiposity.

The method of the present invention may comprise the assessment of at least 2, at least 3, at least 4, at least 5, at least 6, or at least 7 biomarkers.

For example, PC-O 44:6 may be assessed together with PC-O 44:4.

PC-O 44:6 may also be assessed together with PC-O 42:4.
PC-O 44:6 may also be assessed together with PC-O 40:4.
PC-O 44:6 may also be assessed together with PC-O 40:3.
PC-O 44:6 may also be assessed together with PC-O 44:4 and PC-O 42:4.
PC-O 44:6 may also be assessed together with PC-O 44:4, PC-O 42:4, and PC-O 40:4.
PC-O 44:6 may also be assessed together with PC-O 44:4, PC-O 42:4, and PC-O 40:3.
PC-O 44:6 may also be assessed together with PC-O 44:4, PC-O 42:4, PC-O 40:3, and PC-O 40:4.
PC-O 44:6 may also be assessed together with PC-O 44:4, PC-O 42:4, PC-O 40:3, PC-O 40:4, and glutamine.
PC-O 44:6 may also be assessed together with PC-O 44:4, PC-O 42:4, PC-O 40:3, PC-O 40:4, glutamine and tyrosine.

The advantage of assessing more than one biomarker is that the more biomarkers are evaluated the more reliable the diagnosis will become. If, e.g., more than 1, 2, 3, 4, 5, 6, or 7 biomarkers exhibit the elevations or decreases in concentration as described above, the predictive power for the presence or absence and the degree of visceral obesity as well as the risk for associated disorders is stronger.

In accordance with this the inventors have identified even further biomarkers that can be used to predict visceral adiposity and the risk to develop associated disorders.

For example, it was found that increased concentrations of phenylalanine, Leucine, Isoleucine, palmitoylcarnitine (C16), caproylcarnitine (C10) octenoylcarnitine (C8:1) lysophosphatidylcholine (LPC) 24:0, phosphatidylcholine (PC)PC 30:0, and/or PC 34:4 in body fluids or decreased concentrations of PC-O 34:1, PC-O 34:2, PC-O 36:2, PC-O 36:3, PC-O 40:6, PC-O 42:2, PC-O 42:3, PC-O 44:3, PC-O 44:5, PC 42:0, and/or PC 42:2 in body fluids compared to corresponding reference values previously obtained indicates an increased visceral adiposity and an increased risk for associated disorders.

PC is phosphatidylcholine. LPC is lysophospatidylcholine. C is acyl carnitine.

Conversely, decreased concentrations of phenylalanine, Leucine, Isoleucine, C10 (decanoyl carnitine), C16 (Palmitoylcarnitine), C8:1 (Octenoyl-Carnitine) LPC 24:0, PC 30:0, and/or PC 34:4 in body fluids or increased concentrations of PC-O 34:1, PC-O 34:2, PC-O 36:2, PC-O 36:3, PC-O 40:6, PC-O 42:2, PC-O 42:3, PC-O 44:3, PC-O 44:5, PC 42:0, and/or PC 42:2 in body fluids compared to corresponding reference values previously obtained indicates a decreased visceral adiposity and a reduced risk for associated disorders.

Hence, the methods of the present invention may, further comprise the steps of determining the level of at least one further biomarker selected from the group consisting of phenylalanine, Leucine, Isoleucine, C10 (decanoyl carnitine), C16 (Palmitoylcarnitine), C8:1 (Octenoyl-Carnitine), LPC 24:0, PC 30:0, PC 34:4, PC-O 34:1, PC-O 34:2, PC-O 36:2, PC-O 36:3, PC-O 40:6, PC-O 42:2, PC-O 42:3, PC-O 44:3, PC-O 44:5, PC 42:0, and/or PC 42:2 in the body fluid sample, and comparing the subject's level of at least one of phenylalanine, Leucine, Isoleucine, C10, C16, C8:1, carnitine, LPC 24:0, PC 30:0, PC 34:4, PC-O 34:1, PC-O 34:2, PC-O 36:2, PC-O 36:3, PC-O 40:6, PC-O 42:2, PC-O 42:3, PC-O 44:3, PC-O 44:5, PC 42:0, and/or PC 42:2 to a predetermined reference value, wherein the predetermined reference value is based on average phenylalanine, Leucine, Isoleucine, C10, C16, C8:1, carnitine, LPC 24:0, PC 30:0, PC 34:4, PC-O 34:1, PC-O 34:2, PC-O 36:2, PC-O 36:3, PC-O 40:6, PC-O 42:2, PC-O 42:3, PC-O 44:3, PC-O 44:5, PC 42:0, and/or PC 42:2 levels in a body fluid sample of a normal healthy control population, or on phenylalanine, Leucine, Isoleucine, C10 (decanoyl carnitine), C16 (Palmitoylcarnitine), C8:1 (Octenoyl-Carnitine), LPC 24:0, PC 30:0, PC 34:4, PC-O 34:1, PC-O 34:2, PC-O 36:2, PC-O 36:3, PC-O 40:6, PC-O 42:2, PC-O 42:3, PC-O 44:3, PC-O 44:5, PC 42:0, and/or PC 42:2 levels in the same body fluid obtained from the same subject previously, and wherein an increased phenylalanine, Leucine, Isoleucine, C10, C16, C8:1, carnitine, LPC 24:0, PC 30:0, and/or PC 34:4 level in the body fluid and/or a decreased PC-O 34:1, PC-O 34:2, PC-O 36:2, PC-O 36:3, PC-O 40:6, PC-O 42:2, PC-O 42:3, PC-O 44:3, PC-O 44:5, PC 42:0, and/or PC 42:2 level in the body fluid sample compared to the predetermined reference values indicates an increased visceral adiposity.

An increased visceral adiposity increases the risk to develop disorders associated with excess visceral fat.

Consequently, in the methods of the present invention the degree of visceral adiposity may be used as indication for the likelihood to develop disorders associated with excess visceral fat.

Also, changes in visceral adiposity may be used as indication for an increased or decreased likelihood to develop disorders associated with excess visceral fat.

Disorders associated with visceral adiposity are for example cardio metabolic disorders.

Hence, the methods of the present invention may be used to determine the risk to develop cardio metabolic disorders.

Further disorders associated with visceral adiposity are for example metabolic deregulations. Typical metabolic deregulations are the following obesity, insulin resistance, Type 2 diabetes, metabolic syndrome, vascular diseases (hypertension, coronary heart disease), steatohepatitis in metabolic liver disease, lipodystrophies, pulmonary function, inflammatory disorders and other obesity related disorders.

The methods of the present invention can be carried out with any subject.

Advantageously, the method of the present invention may be carried out on subjects at risk of developing visceral adiposity and/or disorders associated with visceral adiposity.

For example the methods of the present invention may be to be carried out with normal, overweight or obese subjects.

"Overweight" is defined for an adult human as having a BMI between 25 and 30. "Body mass index" or "BMI" means the ratio of weight in kg divided by the height in meters, squared. "Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

The reference value for PC-O 44:6 and optionally for the other biomarkers is preferably measured using the same units used to characterize the level of PC-O 44:6 and optionally the other biomarkers obtained from the test subject. Thus, if the level of the PC-O 44:6 and optionally the other biomarkers is an absolute value such as the units of PC-O 44:6 in µmol/l (µM) the reference value is also based upon the units of PC-O 44:6 in µmol/l (µM) in individuals in the general population or a selected control population of subjects.

Moreover, the reference value can be a single cut-off value, such as a median or mean. Reference values of PC-O 44:6 and optionally the other biomarkers in obtained body fluid samples, such as mean levels, median levels, or "cut-off" levels, may be established by assaying a large sample of individuals in the general population or the selected population and using a statistical model such as the predictive value method for selecting a positively criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is incorporated herein by reference.

Skilled artesians will know how to assign correct reference values as they will vary with gender, race, genetic heritage, health status or age, for example.

As an example the inventors have determined typical reference values in obese adult human subjects and in normal adult human subjects in a body fluid such as blood plasma, for example.

Consequently, the predetermined mean reference values for obese subjects may be about
68.71 µM body fluid for tyrosine,
662.67 µM body fluid for glutamine,
1.47 µM body fluid for PC-O 44:6,
0.84 µM body fluid for PC-O 44:4,
1.27 µM body fluid for PC-O 42:4,
2.65 µM body fluid for PC-O 40:4,
1.37 µM body fluid for PC-O 40:3,
52.97 µM body fluid for phenylalanine,
193.56 µM body fluid for Leucine+Isoleucine,
0.19 µM body fluid for C10,
0.06 µM body fluid for C16,
0.03 µM body fluid for C8:1,
0.25 µM body fluid for LPC 24:0,
4.18 µM body fluid for PC 30:0,
1.11 µM body fluid for PC 34:4,
9.84 µM body fluid for PC-O 34:1,
11.49 µM body fluid for PC-O 34:2,
11.79 µM body fluid for PC-O 36:2,
7.20 µM body fluid for PC-O 36:3,
3.68 µM body fluid for PC-O 40:6,
0.56 µM body fluid for PC-O 42:2,
0.89 µM body fluid for PC-O 42:3,
0.21 µM body fluid for PC-O 44:3,
2.17 µM body fluid for PC-O 44:5,
0.56 µM body fluid for PC 42:0,
0.22 µM body fluid for PC 42:2.

In normal subjects the predetermined mean reference values may be about
75.00 µM body fluid for tyrosine,
748.27 µM body fluid for glutamine,
1.21 µM body fluid for PC-O 44:6,
0.50 µM body fluid for PC-O 44:4,
1.12 µM body fluid for PC-O 42:4,
3.24 µM body fluid for PC-O 40:4,
2.10 µM body fluid for PC-O 40:3,
49.17 µM body fluid for phenylalanine,
197.52 µm body fluid for Leucine+Isoleucine,
0.29 µM body fluid for C10,
0.09 µM body fluid for C16,
0.04 µM body fluid for C8:1,
0.77 µM body fluid for LPC 24:0,
4.10 µM body fluid for PC 30:0,
1.42 µM body fluid for PC 34:4,
8.20 µM body fluid for PC-O 34:1,
9.26 µM body fluid for PC-O 34:2,
12.67 µM body fluid for PC-O 36:2,
5.83 µM body fluid for PC-O 36:3,
4.45 µM body fluid for PC-O 40:6,
0.82 µM body fluid for PC-O 42:2,
1.08 µM body fluid for PC-O 42:3,
0.22 µM body fluid for PC-O 44:3,
1.82 µM body fluid for PC-O 44:5,
0.65 µM body fluid for PC 42:0,
0.35 µM body fluid for PC 42:2.

The subjects to be tested with the method of the present invention may be a human or an animal, in particular a mammal, for example. Typical animals may be companion animals, such as cats or dogs of farm animals, for example.

Those skilled in the art will understand that they can freely combine all features of the present invention described herein, without departing from the scope of the invention as disclosed. In particular, features described for the methods of the present invention may be applied to other methods and to the use of the present invention and vice versa.

Further advantages and features of the present invention are apparent from the following Examples and Figures.

Table 1 shows clinical characteristics of the recruited cohort as stratified in four quartiles based on their visceral fat content as assessed by the $\log_{10}$ value of the intraperitoneal/abdominal fat ratio measured by computerized tomography. Values are presented as mean (±SD). ALAT=alanine aminotransferase, ASAI=aspartate aminotransferase, BMI=body mass index, GGT=gamma-glutamyl transpeptidase, HDL-C=high density lipoprotein cholesterol, HOMA-IR=homeostasis model assessment of insulin resistance, LDL-C=low density lipoprotein cholesterol, MAP=mean arterial blood pressure, NEFAs=non esterified fatty acids, TG=triglycerides.

Table 2 shows metabolite concentrations presented as mean (±SD) for each of the four quartiles based on their visceral fat content as assessed by the $\log_{10}$ value of the intraperitoneal/abdominal fat ratio measured by computerized tomography.

FIG. 1 shows the statistical reconstruction of $^1$H NMR blood plasma profiles using random forest analysis to identify metabolic patterns associated with visceral adiposity (as identified with squared boxes). GPCs=glycerophospholipids, PUFAs=polyunsaturated fatty acids, UFAs=unsaturated fatty acids.

Figure 2:
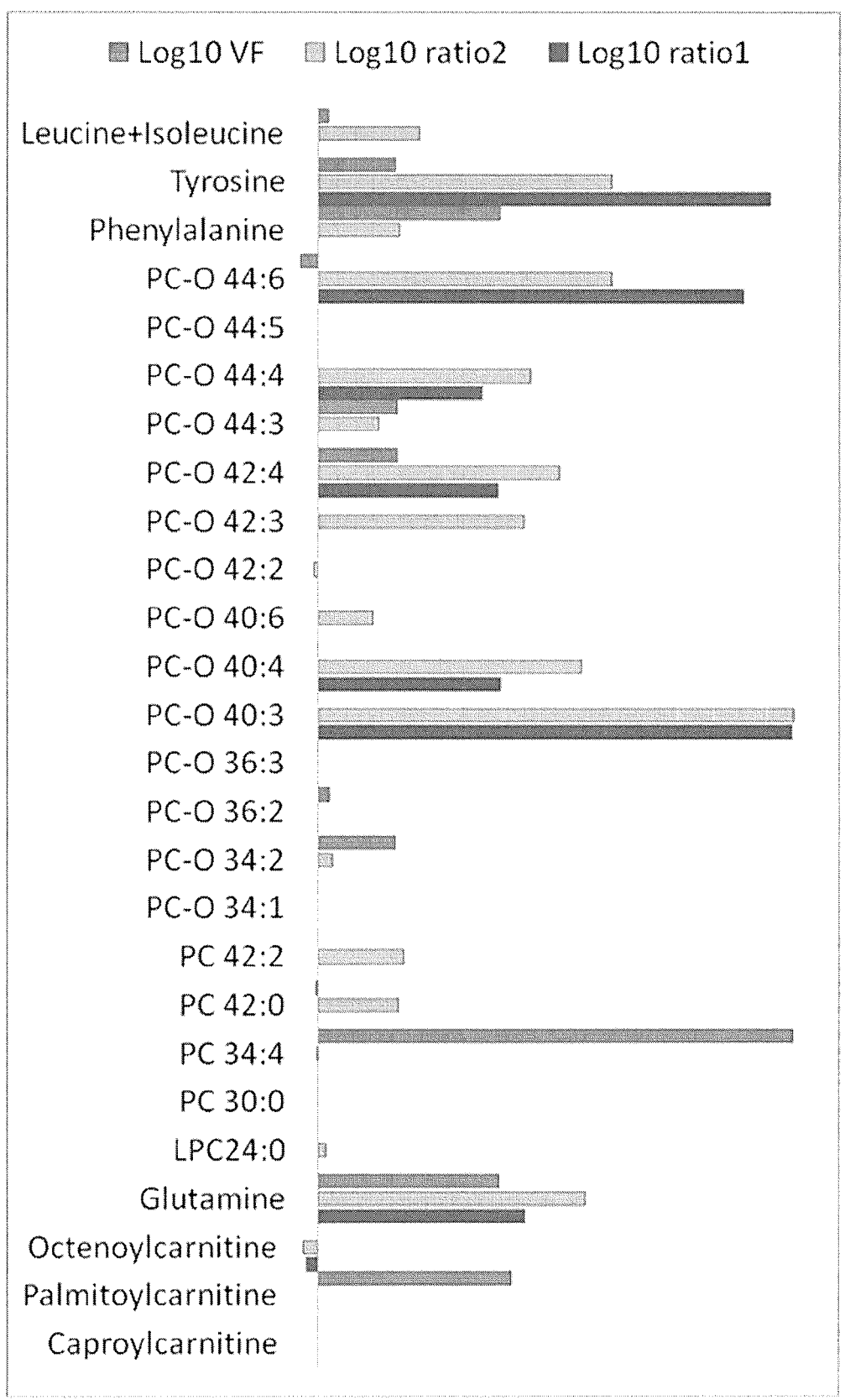

FIG. 2 shows metabolite importance and robustness in predicting visceral fat adiposity as assessed by Random forest analysis. Pooled mean decrease in accuracy after n=10000 random forest generations. Higher variable importance corresponds to higher values of pooled mean decrease in accuracy.

Figure 3A:
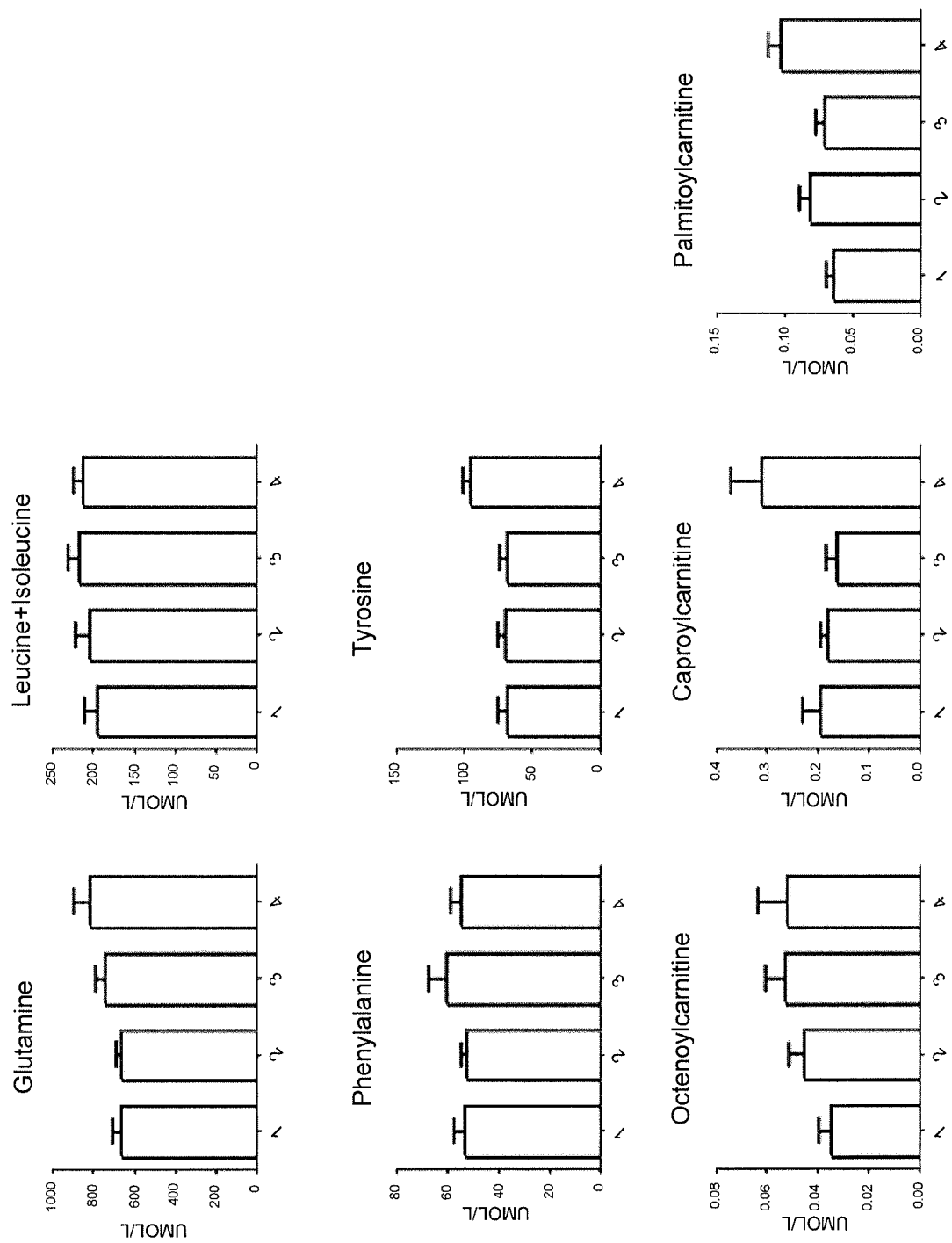
Figure 3B:
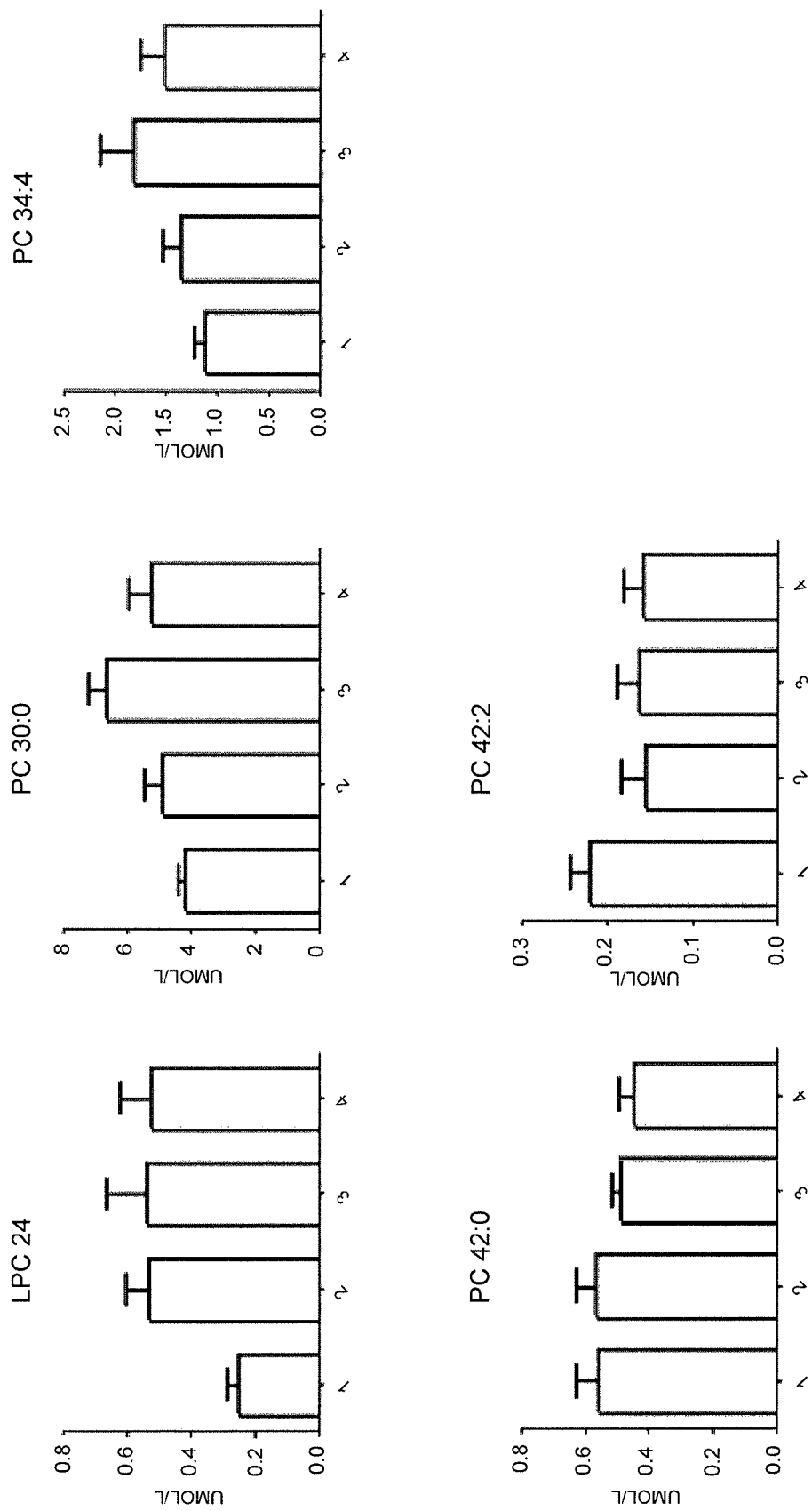
Figure 3C:
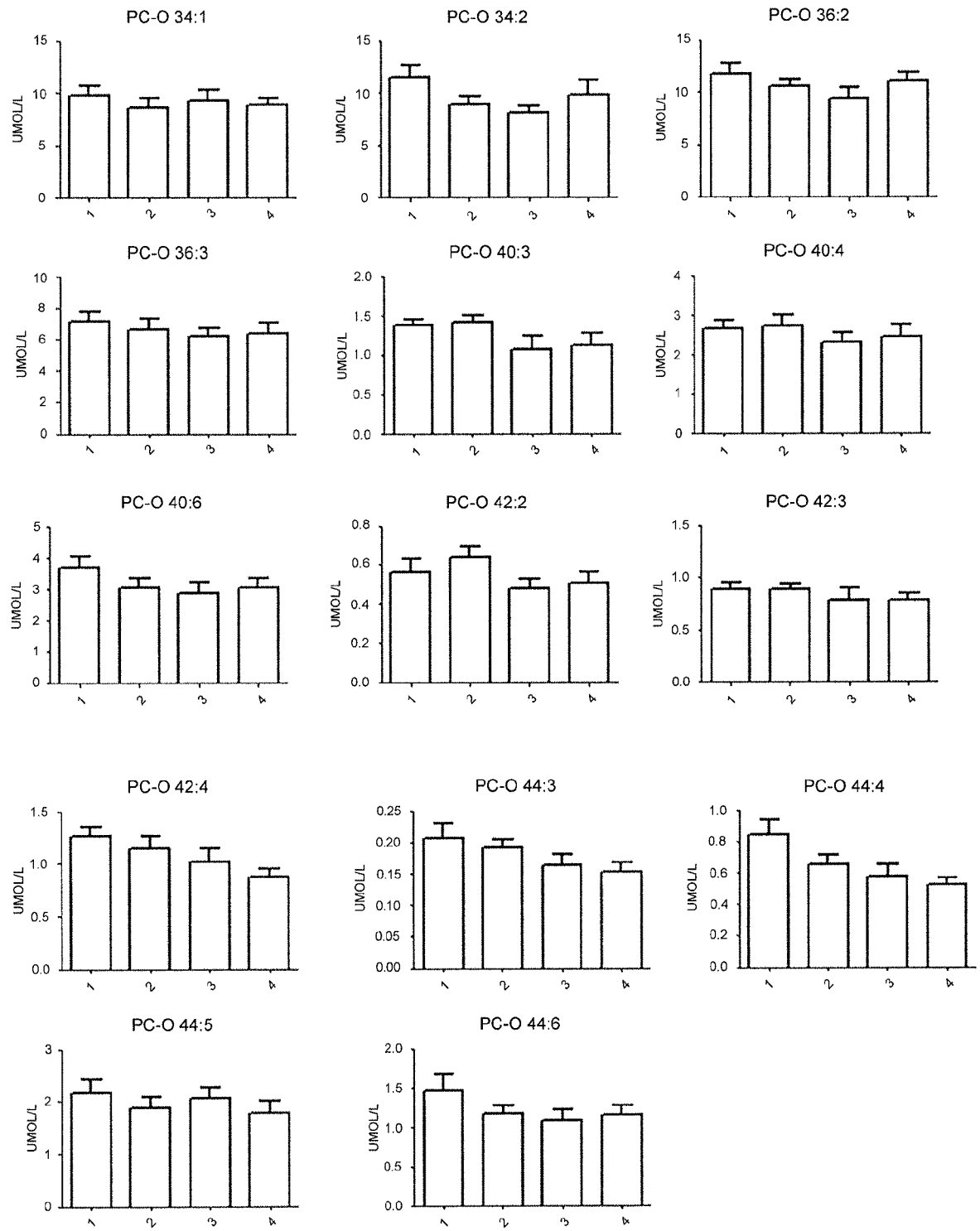

FIGS. 3A, 3B and 3C show metabolite differences between high and low visceral fat subjects for each selected metabolite. Data are plotted for each quartile based on their visceral fat content as assessed by the $\log_{10}$ value of the intraperitoneal fat volume measured by computerized tomography, 1=quartile 1, 2—quartile 2, 3=quartile 3, 4=quartile 4.

EXAMPLES

Subjects and Experimental Design

The clinical trial was an observational study conducted on 40 healthy obese Caucasian women at the Centre Hospitalier Universitaire Vaudois (CHUV, Lausanne, Switzerland). The study protocol was approved by an independent Ethical Committee located at the CHUV. The participants had a BMI between 28 and 40, aged between 25 and 45 years old, and showed no metabolic disease traits (diabetes type 2, cardiovascular disease or metabolic syndrome). The resulting biological samples (blood plasma and 24 hours urine samples) were stored at −80° C. until metabolomic analysis.

Body Composition Assessment

Full body scan was performed to determine both abdominal fat distribution and total body composition. Total body scans were made on a GE Lunar iDXA system (software version: enCORE version 12.10.113) with scan mode automatically determined by the device. For the DXA measurement, all subjects were wearing a hospital gown and had all metal artifacts removed. The iDXA unit was calibrated daily using the GE Lunar calibration phantom. A trained operator performed all scans following the operator's manual for patient positioning and data acquisition. During the one-hour appointment, total body scans of each subject were performed twice with repositioning between scans. Scans were analyzed with the enCORE software (version 14.00.207). The ROIs were automatically determined by the enCORE software (Auto ROI) for total body, arms, legs, trunk, android, and gynoid regions. An experienced DXA operator also verified and, when indicated, repositioned the ROI placements (Expert ROI). In addition to iDXA scan, waist and hip measurements were performed.

The CT measures were performed on 64 multi-detector CT scanner (VCT Lightspeed, GE Medical Systems, Milwaukee, USA). Subjects lied in the supine position with their arms above their head and legs elevated with a cushion. A single scan (10 mm) of the abdomen is acquired at the level of L4-L5 vertebrae and analyzed for a cross-sectional area of adipose tissue, expressed in square centimeters. The following acquisition parameters were used: 120 Kv, 100-200 mA with z-axis dose modulation and a field of view 500 mm. Axial transverse images of 5 mm slice thickness are reconstructed using a standard kernel. The quantification process uses a semi interactive commercially available algorithm for segmentation of subcutaneous and intra-abdominal fat on the Advantage Window workstation (GE Medical Systems).

Clinical Chemistry.

Plasma total, HDL and LDL cholesterol, triglycerides, urates, creatinine, sodium and potassium concentrations, ALAT, ASAT, GGT, glucose, non-esterified fatty acids, insulin and mean arterial blood pressure (MAP) were determined using routine laboratory methods. Insulin resistance status was assessed as homeostasis model assessment of insulin resistance (HOMA-IR) according to the previously described formula (Mathews et al., 1985): insulin (μU/mL)×glucose (mmol/L)/22.5.

Sample Preparation and $^1$H-NMR Spectroscopic Analysis

Heparin blood plasma samples (400 μL) were introduced into 5 mm NMR tubes with 200 μL of deuterated phosphate buffer solution (KH2PO4 with a final concentration of 0.2M). Deuterium was employed as locking substance. Metabolic profiles were measured on a Bruker Avance III 600 MHz spectrometer equipped with an inverse 5 mm cryogenic probe at 300 K (Bruker Biospin, Rheinstetten, Germany). Standard $^1$H-NMR one-dimensional pulse sequence with water suppression (RD=4s), Carr-Purcell-Meiboom-Gill (CPMG) spin-echo sequence with water suppression (RD=4s), and diffusion-edited sequence (RD=4s) where acquired for each plasma sample. For each one dimensional experiment 32 scans were collected using 98 K data points. $^1$H-NMR spectra were processed using TOPSPIN (version 2.1, Bruker, Germany) software package prior to Fourier transformation. The acquired NMR spectra were manually phased and baseline corrected, and referenced to the chemical shift of the anomeric proton of α-glucose at δ5.2396 for plasma spectra. The assignment of the $^1$H-NMR resonances to specific metabolites was achieved by matching our in-house developed NMR database of pure compounds and using literature data (Fan, T. W. (1996) Progress in Nuclear Magnetic Resonance Spectroscopy 28, 161-219; Nicholson, J. K., et al. (1995) Anal. Chem. 67, 793-811). Metabolite identification was confirmed by 2D $^1$H-$^1$H COrrelation SpectroscopY (COSY) (Hurd, R. E. (1990) J. Magn. Reson. 87, 422-428), $^1$H-$^1$H TOtal Correlation SpectroscopY (TOCSY) (Bax, A. & Davis (1985) J. Magn. Reson. 65, 355-360) and $^1$H-$^{13}$C Heteronuclear Single Quantum Correlation (HSQC) (Bodenhausen, G. & Ruben (1980) Chemical Physics Letters 69, 185-189) NMR techniques.

Sample Preparation for Biocrates Life Sciences Absolute IDQ™ Kit Analysis

The Biocrates Life Sciences AbsoluteIDQ™ kit was used for EDTA plasma samples as previously published (Römisch- Margl, W., C. Prehn, R. Bogumil, C. Rohring, K. Suhre, J. Adamski, Procedure for tissue sample preparation and metabolite extraction for high-throughput targeted metabonomics. Metabonomics, 2011. Online First). Well plate preparation and sample application and extraction were carried out according to the manufacturer's instructions. A final volume of 10 μl of plasma was loaded onto the provided 96-well plate, containing isotopically labeled internal standards. Liquid chromatography was realized on a Dionex Ultimate 3000 ultra high pressure liquid chromatography (UHPLC) system (Dionex AG, Olten, Switzerland) coupled to a 3200 Q TRAP mass spectrometer (AB Sciex; Foster City, Calif., USA) fitted with a TurboV ion source operating in electrospray ionization (ESI) mode. Sample extracts (20 μl) were injected two times (in positive and negative ESI modes) via direct infusion using a gradient flow rate of 0-2.4 min: 30 μl/min, 2.4-2.8 min: 200 μl/min, 2.9-3 min: 30 μl/min. MS source parameters were set at: desolvation temperature (TEM): 200° C., high voltage: −4500 V (ESI−), 5500 V (ESI+), curtain (CUR) and nebuliser (GS1 and GS2) gases: nitrogen; 20, 40, and 50 psi; respectively, nitrogen collision gas pressure: 5 mTorr. MS/MS acquisition was realised in scheduled reaction monitoring (SRM) mode with optimised declustering potential values for the 163 metabolites screened in the assay. Raw data files (Analyst software, version 1.5.1; AB Sciex, Foster City, Calif., USA) were imported into the provided analysis software MetIQ to calculate metabolite concentrations. List of all detectable metabolites is available from Biocrates Life Sciences, Austria (http://biocrates.com).

Multivariate Data Analysis

The plasma NMR spectra were converted into 22K data points over the range of δ0.2-10.0 using an in-house developed MATLAB routine excluding the water residue signal between δ4.68-5.10. Chemical shift intensities were normalized to the sum of all intensities within the specified range prior to chemometric analysis. Chemometric analysis was performed using the software package SIMCA-P+(version 12.0.1, Umetrics AB, Umeå, Sweden) and in-house developed MATLAB (The MathWorks Inc., Natick, Mass., USA) routines. In order to detect the presence of similarities between metabolic profiles, Principal Component Analysis (PCA) (Wold, S., et al. (1987) Chemom. Intell. Lab. Syst. 2, 37-52), Projection to Latent Structures (PLS) (Wold, S., et al. (1987) PLS Meeting, Frankfurt) and the Orthogonal Projection to Latent Structures (O-PLS) (Trygg, J. & Wold (2003) J. Chemom. 17, 53-64) were used. Seven-fold cross validation was used to assess the validity of the model (Cloarec, O., et al. (2005) Anal. Chem. 77, 517-526). The classification accuracy of the O-PLS-DA model was established from the predicted samples in the 7-fold cross-validation cycle.

Targeted MS data was analyzed by Random Forests by using the package 'randomForest' (A. Liaw and M. Wiener (2002). Classification and Regression by randomForest. R News 2(3), 18-22.) running in the R environment (R Development Core Team (2011). R: A language and environment for statistical computing. R Foundation for Statistical Computing, Vienna, Austria. ISBN 3-900051-07-0, URL http://www.R-project.org/.). Univariate significance tests for confirmation were also performed in R.

Due to the non-normal distribution of the visceral adiposity, the following parameters were employed for the subsequent metabolomics analysis: log-transform value of the visceral fat content, of the intraperitoneal/subcutaneous fat ratio (ratio 1), or of the intraperitoneal/abdominal fat ratio (ratio 2).

Anthropometric and biochemical characteristics of the cohort are shown in Table 1, as per stratification in four quartiles (Q1-4, n=10) based on the $\log_{10}$ value of the intraperitoneal/abdominal fat ratio (ratio 2) measured using CT. Fasting glucose ($p<0.10$) and insulin ($p<0.05$), as well as HOMA-IR ($p<0.05$) were higher in the subjects with the highest visceral adiposity (Q4) compared to (Q1). Log-transform values of the intraperitoneal/subcutaneous fat ratio or of the intraperitoneal/abdominal fat ratio were used preferably to stratify subjects according to their visceral adiposity, since these parameters were shown to be independent of BMI, Hipp, Waist, ALAT, MAP, and calorimetric indices, which was not the case for log-transform value of intraperitoneal fat volume. Interestingly in his cohort, HDL, LDL, and total cholesterol were not statistically different between groups.

In order to identify phenotypic signatures of visceral fat deposition, plasma samples were analyzed using $^1$H-NMR and targeted LC-MS/MS metabolomic approach. Analyses were conducted on the fasting plasma samples. OPLS analysis of samples collected showed some subtle but significant associations between blood plasma lipids and visceral fat deposition ($R^2X$: 0.68; $R^2Y$: 0.506; $Q^2Y$: 0.167). Random forest analysis was also employed to confirm the statistical association between specific plasma lipids and visceral fat status (FIG. 1), which suggested a specific plasma lipid remodeling marked by changes in glycerophospholipids and the fatty acid saturation pattern.

Therefore, targeted LC-MS/MS metabonomics was employed to provide structural information and quantitative measures of 163 metabolites, including amino acids, sugars, acylcarnitines, sphingolipids, and glycerophospholipids. Using OPLS analysis, it was possible to determine a metabolic signature of visceral fat adiposity (R2X: 0.29; R2Y: 0.68; Q2Y: 0.32).

To select the more robust markers, there was used the % Mean decrease accuracy of 'out-of-bag' data as variable importance feature. In this way, it was possible to determine the variables that better discriminate subjects according to their visceral fat status (Q1 versus Q4). Both Q1, Q4 were assessed using either log-transform value of the intra peritoneal fat volume, ratio 1 and ratio 2. The modeling was also tested for assessing inter-days metabolic variations, by considering each visit separately (data not shown). Ultimately, 26 metabolites were retained as of importance to classify subjects according to their visceral fat adiposity (FIGS. 2, 3A, 3B, 3C). Visceral adiposity was associated with increasing concentrations of circulating amino acids, including glutamine, leucine/isoleucine, phenylalanine and tyrosine. These patterns were associated with higher concentrations of acylcarnitines, including palmitoylcarnitine (C16), caproylcarnitine (C10) octenoylcarnitine (C8:1), and lysophospatidylcholine LPC 24:0 and diacyl phospholipids, including PC 30:0, PC 34:4. In addition, visceral adiposity was marked by a depletion in acyl ethers PC-O 36:3, PC-O 40:3, PC-O 40:4, PC-O 40:6, PC-O 42:2, PC-O 42:3, PC-O 42:4, PC-O 44:3, PC-O 44:4, PC-O 44:6, and two diacyl phosphopcholines (PC 42:0 and PC 42:2). To assess the individual discriminant ability of each component of the signature, Wilcoxon Rank sum tests among the visceral fat adiposity groups were performed (all metabolites are listed in Table 2 according to the tested descriptor, namely log 10 value of ratio 2).

FIG. 2 summarizes the selected biomarkers together with their weight in the classification of visceral adiposity, using log 10 value of visceral fat content, log 10 value of ratio 1 or log 10 value of ratio 2. These markers showed sensitivity and specificity of 0.90 for visceral fat in cross-validation mode (Sencv, Specv).

TABLE 1

| Factor | First Quartile Q1 | Second Quartile Q2 | Third Quartile Q3 | Fourth Quartile Q4 | Mann-Whitney P values (Q1-Q4) |
|---|---|---|---|---|---|
| Age, years | 33.90 ± 4.89 | 32.80 ± 3.58 | 38.00 ± 4.42 | 37.60 ± 5.82 | 0.13897 |
| BMI, kg/m2 | 34.01 ± 3.27 | 36.34 ± 3.62 | 37.00 ± 2.95 | 34.59 ± 4.42 | 0.93969 |
| Log10 intraperitoneal/abdominal fat ratio | −0.70 ± 0.05 | −0.61 ± 0.02 | −0.52 ± 0.02 | −0.40 ± 0.06 | 1.25506E−09 |
| Hipp, cm | 122 ± 5.47 | 128 ± 7.48 | 127.34 ± 6.29 | 122.28 ± 9.65 | 0.56498 |
| Waist, cm | 97.28 ± 8.28 | 103.39 ± 8.7 | 108.72 ± 11.71 | 104.73 ± 13.84 | 0.45838 |
| Waist/Hipp ratio | 0.80 ± 0.07 | 0.81 ± 0.06 | 0.85 ± 0.07 | 0.84 ± 0.09 | 0.35104 |
| Na, mmol/L | 140.40 ± 1.35 | 140.80 ± 1.32 | 141.50 ± 1.58 | 139.9 ± 1.10 | 0.32894 |
| K, mmol/L | 4.05 ± 0.18 | 4.10 ± 0.18 | 3.99 ± 0.25 | 4.04 ± 0.18 | 0.87656 |
| Glucose, mmol/L | 4.95 ± 0.35 | 5.17 ± 0.52 | 5.41 ± 0.49 | 5.37 ± 0.5 | 0.05716 |
| Creatinine, mmol/L | 65.60 ± 9.45 | 65.2 ± 11.2 | 64.78 ± 9.28 | 70.3 ± 6.53 | 0.2563 |
| Cholesterol, mmol/L | 5.52 ± 1.01 | 5.58 ± 0.85 | 5.31 ± 0.68 | 5.48 ± 0.97 | 0.90965 |
| HDL, mmol/L | 1.54 ± 0.43 | 1.32 ± 0.29 | 1.38 ± 0.25 | 1.32 ± 0.24 | 0.18104 |
| HDL/Chol ratio | 3.77 ± 1.07 | 4.42 ± 1.22 | 3.99 ± 0.97 | 4.24 ± 0.95 | 0.28901 |
| LDL, mmol/L | 3.50 ± 0.97 | 3.56 ± 0.88 | 3.34 ± 0.61 | 3.47 ± 0.79 | 1 |
| TG, mmol/L | 1.04 ± 0.43 | 2.25 ± 2.1 | 1.28 ± 0.45 | 1.52 ± 0.57 | 0.09354 |
| Urates, μmol/L | 275.20 ± 41.93 | 263.22 ± 71.45 | 303.40 ± 75.28 | 285.00 ± 31.70 | 0.35268 |
| ASAT, U/L | 21.40 ± 3.24 | 21.4 ± 4.48 | 24.00 ± 6.94 | 24.50 ± 6.7 | 0.40157 |
| ALAT, U/L | 18.40 ± 6.11 | 19.20 ± 5.07 | 23.50 ± 8.34 | 27.10 ± 13.28 | 0.13971 |
| ALAT/ASAT ratio | 0.86 ± 0.25 | 0.91 ± 0.21 | 0.99 ± 0.3 | 1.08 ± 0.34 | 0.12066 |
| MAP, mmHg | 57.80 ± 18.6 | 71.10 ± 19.75 | 62.40 ± 20.97 | 57.80 ± 14.15 | 0.8796 |
| GGT, U/L | 20.00 ± 11.86 | 17.50 ± 6.88 | 21.10 ± 4.84 | 25.44 ± 11.26 | 0.19122 |
| Calorimetry, kcal/24 h | 1357.00 ± 191.78 | 1434.00 ± 142.61 | 1469.00 ± 152.49 | 1433.00 ± 210.82 | 0.36362 |
| Insulin | 18.60 ± 9.21 | 22.12 ± 6.32 | 24.36 ± 7.22 | 25.44 ± 4.62 | 0.01468 |
| HOMA-IR | 4.24 ± 2.02 | 4.95 ± 1.49 | 6.06 ± 1.87 | 6.12 ± 1.23 | 0.01149 |
| NEFAs, μmol/L | 544.50 ± 201.51 | 580.60 ± 301.38 | 596.20 ± 185.79 | 585.10 ± 188.62 | 0.66426 |

TABLE 2

| Metabolites | First Quartile Q1 | Second Quartile Q2 | Third Quartile Q3 | Fourth Quartile Q4 | Mann-Whitney P values (Q1-Q4) |
|---|---|---|---|---|---|
| Glutamine, μmol/L | 615.56 ± 107.95 | 748 ± 193.49 | 792.1 ± 260.61 | 714 ± 94.03 | 0.02468 |
| Tyrosine, μmol/L | 61.97 ± 11.02 | 80.54 ± 22.21 | 75.91 ± 21.83 | 80.99 ± 24.69 | 0.05347 |
| Caproylcarnitine, μmol/L | 0.22 ± 0.1 | 0.2 ± 0.09 | 0.14 ± 0.06 | 0.3 ± 0.19 | 0.40018 |
| Palmitoylcarnitine, μmol/L | 0.07 ± 0.02 | 0.07 ± 0.03 | 0.07 ± 0.03 | 0.1 ± 0.04 | 0.12065 |
| Octenoylcarnitine, μmol/L | 0.04 ± 0.02 | 0.05 ± 0.02 | 0.05 ± 0.04 | 0.05 ± 0.02 | 0.25258 |
| LPC 24:0, μmol/L | 0.36 ± 0.25 | 0.51 ± 0.24 | 0.52 ± 0.36 | 0.46 ± 0.31 | 0.21613 |
| PC 30:0, μmol/L | 4.43 ± 1.48 | 5.17 ± 2.35 | 5.75 ± 1.98 | 5.57 ± 1.76 | 0.1564 |
| PC 34:4, μmol/L | 1.3 ± 0.46 | 1.53 ± 1.14 | 1.41 ± 0.52 | 1.55 ± 0.75 | 0.31537 |
| PC 42:0, μmol/L | 0.65 ± 0.23 | 0.48 ± 0.16 | 0.47 ± 0.08 | 0.48 ± 0.14 | 0.07889 |
| PC 42:2, μmol/L | 0.2 ± 0.06 | 0.19 ± 0.11 | 0.13 ± 0.05 | 0.17 ± 0.08 | 0.40018 |
| PC-O 34:1, μmol/L | 9.94 ± 2.22 | 9.78 ± 3.84 | 8.48 ± 2.15 | 8.53 ± 0.99 | 0.17752 |
| PC-O 34:2, μmol/L | 10.66 ± 3.5 | 9.31 ± 3.51 | 9.38 ± 4.57 | 8.77 ± 1.76 | 0.21102 |
| PC-O 36:2, μmol/L | 11.29 ± 2.64 | 11.86 ± 2.68 | 10.38 ± 3.08 | 9.17 ± 2.09 | 0.07865 |
| PC-O 36:3, μmol/L | 7.04 ± 1.68 | 6.7 ± 2.61 | 7.11 ± 1.82 | 5.5 ± 1.24 | 0.02792 |
| PC-O 40:3, μmol/L | 1.41 ± 0.27 | 1.46 ± 0.38 | 1.27 ± 0.3 | 0.86 ± 0.42 | 0.00421 |
| PC-O 40:4, μmol/L | 2.79 ± 0.56 | 2.9 ± 0.73 | 2.47 ± 0.69 | 2.02 ± 0.83 | 0.01784 |
| PC-O 40:6, μmol/L | 3.81 ± 0.86 | 3.27 ± 1.09 | 2.8 ± 0.84 | 2.74 ± 1.09 | 0.06525 |
| PC-O 42:2, μmol/L | 0.66 ± 0.23 | 0.56 ± 0.14 | 0.53 ± 0.16 | 0.45 ± 0.18 | 0.05347 |
| PC-O 42:3, μmol/L | 0.89 ± 0.2 | 0.92 ± 0.14 | 0.9 ± 0.27 | 0.63 ± 0.26 | 0.06525 |
| PC-O 42:4, μmol/L | 1.34 ± 0.33 | 1.09 ± 0.28 | 1.09 ± 0.37 | 0.82 ± 0.22 | 0.00298 |
| PC-O 44:3, μmol/L | 0.21 ± 0.06 | 0.2 ± 0.04 | 0.15 ± 0.06 | 0.17 ± 0.05 | 0.1564 |
| PC-O 44:4, μmol/L | 0.8 ± 0.3 | 0.67 ± 0.24 | 0.63 ± 0.19 | 0.51 ± 0.18 | 0.01721 |
| PC-O 44:5, μmol/L | 2.29 ± 0.74 | 2.03 ± 0.55 | 1.9 ± 0.74 | 1.71 ± 0.7 | 0.04113 |
| PC-O 44:6, μmol/L | 1.52 ± 0.56 | 1.22 ± 0.3 | 1.11 ± 0.5 | 1.03 ± 0.32 | 0.01013 |
| Phenylalanine, μmol/L | 49.9 ± 14.16 | 50.47 ± 8.45 | 62.82 ± 22.17 | 56.42 ± 8.38 | 0.04113 |
| Leucine + Isoleucine, μmol/L | 181.44 ± 53.02 | 214.2 ± 56.71 | 202.4 ± 27.39 | 228.8 ± 33.83 | 0.04536 |

What is claimed is:

1. A method of diagnosing the effect of a change in lifestyle on visceral adiposity in a subject, comprising:
   determining a level of 1-0-alkyl-2-acylglycerophosphocholine (PC-O) 44:6 in a body fluid sample obtained from a subject after a change in lifestyle, and
   comparing the subject's PC-O 44:6 level to a predetermined reference value,
   wherein the predetermined reference value is based on a PC-O 44:6 level in the same body fluid obtained from the same subject before the change in lifestyle, and
   wherein an increased PC-O 44:6 level in the sample compared to the predetermined reference value indicates a positive effect of the change in lifestyle on visceral adiposity.

2. The method in accordance with claim 1, wherein the change in lifestyle is a change in diet.

3. The method in accordance with claim 2, wherein the change in diet comprises use of at least one nutritional product that was previously not consumed or consumed in different amounts.

4. The method in accordance with claim 2, wherein the method serves to detect the effectiveness of a new nutritional regimen.

5. The method in accordance with claim 1, wherein the level of PC-O 44:6 in the sample and the predetermined reference value are determined by $^1$H-NMR and/or mass spectrometry.

6. The method in accordance with claim 1, wherein the body fluid is blood plasma or serum.

7. The method in accordance with claim 1, wherein the subject is normal, overweight or obese.

8. The method in accordance with claim 1, wherein the subject is a human or a companion animal.

9. The method in accordance with claim 8, wherein the companion animal is a cat or a dog.

\* \* \* \* \*